United States Patent [19]

Huth et al.

[11] Patent Number: 4,826,851
[45] Date of Patent: May 2, 1989

[54] 2-SUBSTITUTED ERGOLINE UREA AND THIO-UREA DERIVATIVES HAVING NEUROLYPTIC/DOPAMINERGIC ACTIVITY

[75] Inventors: Andreas Huth; Gerhard Sauer; Helmut Wachtel, all of Berlin, Fed. Rep. of Germany

[73] Assignee: Schering Aktiengesellschaft, Berlin and Bergkamen, Fed. Rep. of Germany

[21] Appl. No.: 915,356

[22] Filed: Oct. 6, 1986

[30] Foreign Application Priority Data

Oct. 4, 1985 [DE] Fed. Rep. of Germany ....... 3535930

[51] Int. Cl.$^4$ .................. A61K 31/48; C07D 457/12
[52] U.S. Cl. ................... 514/288; 514/256; 544/333; 546/68
[58] Field of Search ........... 544/333; 514/256, 288; 546/68

[56] References Cited

U.S. PATENT DOCUMENTS

| | | | |
|---|---|---|---|
| 3,029,243 | 4/1962 | Olin | 546/68 |
| 3,251,846 | 5/1966 | Semonsky et al. | 546/68 |
| 3,821,226 | 6/1974 | Fehu et al. | 514/288 |
| 3,953,454 | 4/1976 | Zikan et al. | 546/68 |
| 4,382,940 | 5/1983 | Bernardi et al. | 546/68 |
| 4,500,712 | 2/1985 | Bernardi et al. | 546/68 |

FOREIGN PATENT DOCUMENTS

| | | |
|---|---|---|
| 56358 | 7/1982 | European Pat. Off. . |
| 118848 | 9/1984 | European Pat. Off. . |
| 0160842 | 4/1985 | European Pat. Off. . |
| 3413657 | 10/1985 | Fed. Rep. of Germany . |
| 3413659 | 10/1985 | Fed. Rep. of Germany . |

OTHER PUBLICATIONS

Berde et al., Ergot Alkaloids and Related Compounds, Springer-Verlag, New York (1978), pp. 74, 469–470.
Pratt et al., Organosilicon Compounds, XX, J. Org. Chem., vol. 40 (1975), pp. 1090–1093.

Primary Examiner—Robert Gerstl
Assistant Examiner—Cecilia Shen
Attorney, Agent, or Firm—Millen & White

[57] ABSTRACT

Novel 2-substituted ergolinyl urea and thioruea derivatives are disclosed, as well as their use as pharmaceuticals, specifically as neuroleptics. The compounds, which possess central dopaminergic activity, have the formula

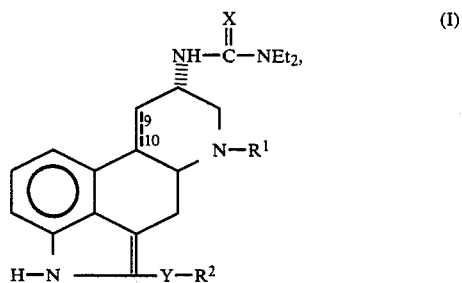

wherein
  X is an oxygen or sulfur atom,
  $R^1$ is a lower alkyl group,
  Y is a sulfur atom, S—CH$_2$—, C$_2$H$_4$—, —CH=CH—, or —C≡C—,
  $R^2$ is an aromatic ring of 5–6 atoms, 0–3 of which are O, S or N; or an aromatic ring of 5–6 atoms, 0–3 of which are O, S or N, and which is substituted by C$_{1-2}$-alkyl, C$_{1-2}$-alkoxy, nitrile, nitro, amino, C$_{1-2}$-alkylamino, carbonylamino or halo group, and
  C$_9$C$_{10}$ is a CC-single or a CC-double bond and, if C$_9$C$_{10}$ means a CC-single bond, the hydrogen atom in the 10-position is in the α-location,
or a pharmaceutically acceptable acid addition salt thereof, wherein, if X is an oxygen atom, $R^1$ is methyl and C$_9$C$_{10}$ is a single bond, Y—R$^2$ does not mean —C$_2$H$_4$-phenyl or —C≡C—phenyl.

10 Claims, No Drawings

2-SUBSTITUTED ERGOLINE UREA AND THIO-UREA DERIVATIVES HAVING NEUROLYPTIC/DOPAMINERGIC ACTIVITY

The invention relates to novel 2-substituted ergoline derivatives of general Formula I, their preparation, and their use as medicines.

The compounds of this invention have the general Formula I

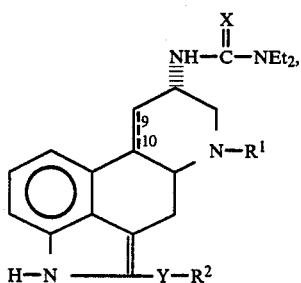

wherein
X is an oxygen or sulfur atom,
$R^1$ is a lower alkyl group,
Y is a sulfur atom, an S—$CH_2$—group, a $C_2H_4$—, a —CH=CH—, or a —C≡C—group,
$R^2$ is an optionally substituted aromatic, and
$C_9$===$C_{10}$ is a CC-single or a CC-double bond and, if $C_9$===$C_{10}$ means a CC-single bond, the hydrogen atom in the 10-position is in the α-location, as well as the acid addition salts thereof, wherein, if X is an oxygen atom, $R^1$ is methyl and $C_9$===$C_{10}$ is a single bond, Y—$R^2$ does not mean $C_2H_4$-phenyl or C≡C-phenyl.

The lower alkyl residues are understood to mean those of up to 6 carbon atoms, $C_1$-$C_4$-alkyls being preferred, such as, for example, methyl, ethyl, isopropyl, n-propyl, n-butyl, isobutyl, and tert-butyl.

The aromatic $R^2$ contains up to 6 carbon atoms wherein one or several (e.g., up to 3) carbon atoms can be substituted by hetero atoms, such as oxygen, sulfur or nitrogen. Examples for suitable aromatic and heteroaromatic residues are: phenyl, pyridinyl, thiophenyl, furanyl, pyrimidinyl, imidazolyl, pyrazolyl, and others.

The aromatic can be mono- or polysubstituted in any desired position, for example with lower alkyl, lower alkoxy, nitrile, nitro, amine, lower alkylamine, carbonylamine, halogen, such as fluorine, chlorine, bromine or iodine, and other substituents.

The lower alkyl groups in $R^2$ have, in particular, 1-2 carbon atoms.

The salts of the compounds of this invention according to Formula I are acid addition salts and are derived from conventionally used acids. Such acids are, for example, inorganic acids, such as, for example, hydrochloric acid, nitric acid, phosphoric acid, sulfuric acid, hydrobromic acid, hydriodic acid, nitrous acid or phosphorous acid, or organic acids, e.g. aliphatic mono- or dicarboxylic acids, phenyl-substituted alkanecarboxylic acids, hydroxyalkanecarboxylic acids, or alkenedicarboxylic acids, aromatic acids or aliphatic or aromatic sulfonic acids. Consequently, physiologically acceptable salts of these acids are, for example, the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, tluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, or naphthalene-2-sulfonate.

As compared with conventional ergolines unsubstituted in the 2-position, such as, for example, lisuride or terguride, as well as 1,1-diethyl-3-(2-phenylethynyl-6-methyl-8α-ergolinyl)urea known from European Application No. 160,842 and the analogous 2-phenethyl derivative, the compounds according to this invention of Formula I are distinguished by a central dopaminergic activity.

The central dopaminergic receptor blockage of A was demonstrated in an interaction test with the dopamine receptor agonist apomorphine on mice after a single i.p. pretreatment (parameter: elimination of hypothermia caused by apomorphine 5 mg/kg i.p.). Male NMRI mice were pretreated with various doses of A which themselves do not affect thermoregulation of the test animals, and, respectively, with a carrier medium. Thirty minutes later, all animals received apomorphine 5 mg/kg i.p. Rectal temperature was measured with the aid of a thermal probe 60 minutes after administration of A and, respectively, of carrier medium (=30 minutes after apomorphine). While the mice pretreated with carrier medium showed hypothermia, the effect of apomorphine of lowering body temperature was overcome in dependence on the dose in animals pretreated with A. (A=compound)

Based on these pharmacological findings, the compounds of the invention can be used as neuroleptics for the treatment of psychoses of the schizophrenic array of symptoms.

The compounds of general Formula I are prepared according to methods known per se.

For example, compounds of general Formula I wherein Y means a sulfur atom or an S—$CH_2$—group can be produced by introducing a blocking group into a 2-haloergoline derivative in the 1-position, then exchanging halogen in the 2-position against lithium, and reacting the thus-obtained 2-lithium ergoline derivative of general Formula II

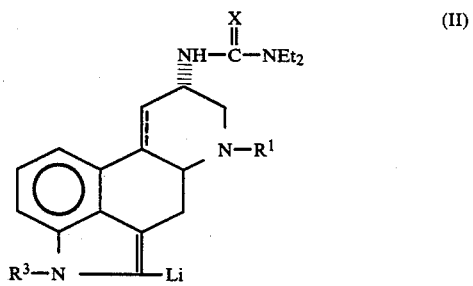

wherein X and $R^1$ have the meanings given above and $R^3$ means a customary blocking group, with a sulfur electrophile and splitting off the blocking group and optionally converting the ureas into the thioureas and- /or forming the physiologically compatible acid addition salt.

The preparation of the compounds of general Formula II has been disclosed, for example, in European Patent Application No. 85104073.3. (European Patent No. 160,842).

For using the compounds of this invention as medicinal agents, they can be brought into the form of a pharmaceutical preparation containing, in addition to the active agent, pharmaceutical, organic or inorganic, inert excipients suitable for enteral or parenteral administration, such as, for example, water, gelatin, gum arabic, lactose, amylose, magnesium stearate, talc, vegetable oils, polyalkylene glycols, etc. The pharmaceutical preparations can be present in solid form, e.g., as tablets, dragees, suppositories, capsules, or in the liquid form, for example as solutions, suspensions or emulsions. Optionally, they contain moreover auxiliary materials, such as preservatives, stabilizers, wetting agents or emulsifiers, salts for altering osmotic pressure, or buffers.

Thus, the pharmacologically active compounds of this invention can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine carbohydrates such as lactose, amylose or starch, magnesium sterate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservative, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

Generally, the compounds of this invention are dispensed in unit dosage form comprising 0.1 to 10 mg in a pharmaceutically acceptable carrier per unit dosage.

The dosage of the compounds according to this invention generally is 0.001 to 1 mg/kg/day, preferably 0.01 to 0.1, when administered to patients, e.g., humans for treatment of psychosis of the schizophrenic array of symptoms, e.g., acute and chronic schizophrenia, especially with negative clinical symptoms, e.g., flattening of response, loss of drive, poverty of speech.

It will be appreciated that the actual preferred amounts of active compound in the specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Preferred sulfur electrophiles that can be mentioned are disulfides, such as, for example, optionally mono- or polysubstituted aromatic disulfides, e.g. diphenyldisulfides and dibenzyldisulfides, or heteroaromatic disulfides with the above-recited heteroaromatic residues.

Electrophilic substitution is effected at low temperatures, preferably between −110° C. to −50° C. in an aprotic solvent.

The reaction mixture of the preceding stage can be utilized in the reaction without a working-up step.

Suitable aprotic solvents are ethers or hydrocarbons, such as, for example, tetrahydrofuran, dioxane, diethyl ether, toluene, hexane, etc.

The blocking group $R^3$ can be any conventionally utilized blocking group, such as, for example, an acyl, arylsulfonyl, or silyl residue, wherein the trialkyl silyl residue, especially the tert-butyldimethylsilyl group, is preferred.

Splitting off of the blocking groups takes place according to the customary methods by treatment with acids, such as dilute mineral acid, trifluoroacetic acid, or inorganic bases, such as KOH, NaOH, or fluoride, such as tetrabutylammonium fluoride, in inert solvents, e.g. water, alcohols, hydrocarbons, etc., at room temperature.

Compounds of general Formula I wherein Y means $—C_2H_4—$, $—CH=CH—$ or $—C\equiv C—$ are prepared by reacting an ergoline derivative of general Formula III

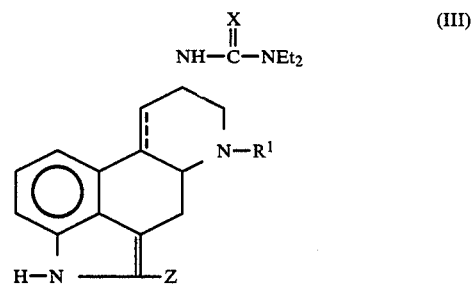

wherein
$R^1$ and X have the meanings given above and
Z is a halogen or $—C\equiv CH$,
in the presence of a catalyst and a base with a compound of the formula halogen-$R^2$ or, respectively, H—C≡C—$R^2$ wherein respectively one reactant represents a halogen-containing compound, and subsequently, if desired, hydrogenating a C≡C-bond partially or entirely, converting the ureas into thioureas and/or forming the acid addition salt. Preparation of the compounds of general Formula III has been described, for example, in EP-A Nos. 160,842, 56,358 and 141,387.

The reaction takes place at temperatures of 0° C. to 120° C., preferably 70° C. to 100° C., in an aprotic solvent, such as, for example, dimethylformamide, N-methylpyrrolidone, tetrahydrofuran, acetonitrile or dioxane.

Preferred catalysts used are palladium compounds, such as palladium salts or palladium complex compounds. Examples that can be cited are palladium(II) acetate, palladium(II) trans-dichlorobis(tri-o-tolylphosphine) or palladium(II) trans-dichlorobis(triphenylphosphine) and palladium(O) tetrakis(triphenylphosphine). The catalyst is utilized in a quantity of 0.01–0.1 mole, based on the 2-haloergoline employed.

An addition of triaryl phosphines enhances the reaction. Catalytic amounts of copper(I) iodide or copper(I) bromide are beneficial for ethynylation.

Suitable bases are secondary and tertiary amines, such as, for example, dimethylamine, diethylamine, piperidine, triethylamine and tri-n-butylamine.

The halogen-containing compound comprises preferably iodine or bromine.

The 2-ethynyl compound can be entirely or partially hydrogenated by catalytically activated hydrogen.

The complete hydrogenation is performed in the presence of a catalyst, such as, for example, Raney nickel or palladium on various supports, such as carbon, at room temperature, optionally under elevated pressure, in an inert solvent, e.g. alcohols, such as methanol, ethanol, propanol, ethers, such as dioxane, diethyl ether, acids such as glacial acetic acid, etc.

Examples of suitable catalysts for the partial hydrogenation to the double bond are palladium salts poisoned, for example, with quinoline or pyridine, but also with lead, or palladium on diverse supports (Lindlar catalysts). Suitable solvents are alcohols or hydrocarbons.

However, conversion of the ethynyl compound into vinyl compounds can also be accomplished by chemical addition of organometallic compounds, e.g. diisobutyl aluminum hydride, and subsequent hydrolysis. Solvents that can be used are hydrocarbons or ethers, such as, for example, hexane, toluene, THF, diethyl ether, etc.

Conversion of the 8α-urea derivatives into the corresponding thiones takes place by reaction with phosphorus oxychloride and subsequent reaction with potassium xanthate. The reaction is conducted at low temperatures with interim temperature elevation in inert solvents, such as ethers.

For the formation of salts, the compounds of Formula I are dissolved in a small amount of methanol or methylene chloride and combined with a concentrated solution of the desired acid in methanol at room temperature.

All reactions are generally performed under a protective gas atmosphere, such as argon or nitrogen, partially under elevated pressure. The starting compounds are known or are prepared in accordance with known methods.

The examples set forth below are to explain the process of this invention.

EXAMPLE 1

1,1-Diethyl-3-(6-methyl-2-phenylthio-8α-ergolinyl)urea

At 0° C., a solution of lithium bis(trimethylsilyl)amide is prepared from 4 ml of anhydrous toluene, 0.32 ml of anhydrous, freshly distilled hexamethyldisilazane (1.5 mmol) and 0.85 ml of n-butyllithium in hexane (1.4 mmol). A solution of 533 mg of 3-[2-bromo-1-(tert-butyldimethylsilyl)-6-methyl-8α-ergolinyl]-1,1-diethylurea (1 mmol) in 50 ml of anhydrous, freshly distilled toluene is added to this solution, and the mixture is stirred for another 15 minutes. After adding 0.8 ml of distilled tetramethylethylenediamine, the mixture is cooled to −90° C., combined with 4.5 ml of tert-butyllithium (6.3 mmol), further stirred for two minutes, and the thus-formed 2-lithium compound is made to react with 2.2 g of diphenyldisulfide (10 mmol), dissolved in 10 ml of anhydrous, freshly distilled toluene, at −70° C. After 30 minutes of agitation at −70° C., water is added, the toluene phase is separated, and the aqueous phase is extracted by shaking with methylene chloride. The organic phases are dried with sodium sulfate and evaporated, the residue is chromatographed on silica gel. The yield is 523 mg of 3-[1-(tertbutyldimethylsilyl)-6-methyl-2-phenylthio-8α-ergolinyl]-1,1-diethylurea (70% of theory). This compound is dissolved in 10 ml of methanol and stirred with 1 ml of 14N potassium hydroxide solution at room temperature for 20 hours. Water is added to this mixture, the latter is stirred in an ice bath for 30 minutes, and the precipitate is suctioned off, yielding 344 mg (82% of theory). Recrystallization from methanol yields 229 mg of the final product (total yield 51%), $[\alpha]_D = +20°$ (0.5% in chloroform).

In a completely analogous way, using dibenzyldisulfide, 3-(2-benzylthio-6-methyl-8α-ergolinyl)-1,1-diethylurea was produced, yield 73%, $[\alpha]_D = -55°$ (0.5% in chloroform), di-(4-methoxyphenyl)disulfide yields 1,1-diethyl-3-[2-(4-methoxyphenylthio)-6-methyl-8α-ergolinyl]urea, di-(4-pyridyl)disulfide yields 1,1-diethyl-3-[6-methyl-2-(4-pyridylthio)-8α-ergolinyl]urea, di-(3-fluorophenyl)disulfide yields 1,1-diethyl-3-[2-(3-fluorophenylthio)-6-methyl-8α-ergolinyl]urea, 3-[2-bromo-1-(tert-butyldimethylsilyl)-9,10-didehydro-6-methyl-8α-ergolinyl]-1,1-diethylurea and diphenyldisulfide give 3-(9,10-didehydro-6-methyl-2-phenylthio-8α-ergolinyl)-1,1-diethylurea in a 43% yield.

The same starting material is reacted with the following electrophiles:

dibenzyldisulfide gives 3-(2-benzylthio-9,10-didehydro-6-methyl-8α-ergolinyl)-1,1-diethylurea in a 52% yield, di-(4-chlorophenyl)disulfide gives 3-[2-(4-chlorophenylthio)-9,10-didehydro-6-methyl-8α-ergolinyl]-1,1-diethylurea, di-(3-methylphenyl)disulfide yields 3-[9,10-didehydro-6-methyl-2-(methylphenylthio)-8α-ergolinyl]-1,1-diethylurea, di-(4-cyanophenyl)disulfide yields 3-[2-(4-cyanophenylthio)-9,10-didehydro-6-methyl-8α-ergolinyl]-1,1-diethylurea, di-(2-pyridyl)disulfide yields 3-[9,10-didehydro-6-methyl-2-(2-pyridylthio)-8α-ergolinyl]-1,1-diethylurea, di-(3-nitrophenyl)disulfide yields 3-[9,10-didehydro-6-methyl-2-(3-nitrophenylthio)-8α-ergolinyl]-1,1-diethylurea, di-(4-aminophenyl)disulfide yields 3-[2-(4-aminophenylthio)-9,10-didehydro-6-methyl-8α-ergolinyl]-1,1-diethylurea, 3-[2-bromo-1-(tert-butyldimethylsilyl)-6-methyl-8α-ergolinyl]-1,1-diethylthiourea and diphenyldisulfide give 1,1-diethyl-3-(6-methyl-2-phenylthio-8α-ergolinyl)thiourea, yield 45%, $[\alpha]_D = +60°$ (0.5% in chloroform), di-(4-aminocarbonylphenyl)disulfide yields 3-[2-(4-aminocarbonylphenylthio)-6-methyl-8α-ergolinyl]-1,1-diethylthiourea, di-(4-fluorophenyl)disulfide yields 1,1-diethyl-3-[2-(4-fluorophenylthio)-6-methyl-8α-ergolinyl]thiourea, 3-[2-bromo-1-(tert-butyldimethylsilyl)-6-n-propyl-8α-ergolinyl]-1,1-diethylurea and diphenyldisulfide yield 1,1-diethyl-3-(2-phenylthio-6-n-propyl-8α-ergolinyl)urea, dibenzyldisulfide gives 3-[2-(benzylthio)-6-propyl-8α-ergolinyl]-1,1-diethylurea, di-(4-pyridyl)disulfide yields 1,1-diethyl-3-[6-n-propyl-2-(4-pyridylthio)-8α-ergolinyl]urea.

EXAMPLE 2

3-[6-Methyl-2-(thien-2-ylethynyl)-8α-ergolinyl]-1,1-diethylurea

Under argon, 72 mg of 3-(6-methyl-2-ethynyl-8α-ergolinyl)-1,1-diethylurea is heated in 2 ml of dimethylformamide with 2 ml of triethylamine, 1.5 mg of copper(I) iodide, 0.069 ml of 2-iodothiophene, and 4.8 mg of palladium(O) tetrakis(triphenylphosphine) for 2 hours to 80° C. After evaporation, the mixture is taken up in ethyl acetate and washed in succession with dilute ammonia solution and saturated sodium chloride solution. After chromatography over silica gel with ethyl acetate:ethanol=1:1 and recrystallization from ethanol/hexane, 26 mg of 3-[6-methyl-2-(thien-2-ylethynyl)-8α-ergolinyl]-1,1diethylurea is obtained, mp 252°–256° C.

The following compounds are prepared analogously:
3-[6-methyl-2-(3-pyridinylethynyl)-8α-ergolinyl]-1,1-diethylurea, mp 226°–229° C., $[\alpha]_D = +124.6°$ (c=0.215; pyridine),
3-[2-(4-methoxyphenylethynyl)-6-methyl-8α-ergolinyl]-1,1-diethylurea, mp 210°–211° C., $[\alpha]_D = +118°$ (c=0.2; pyridine).

EXAMPLE 3

3-[2-(4-Cyanophenylethynyl)-6-methyl-8α-ergolinyl]1,1-diethylurea

Under argon, 200 mg of 3-(2-iodo-6-methyl-8α-ergolinyl)-1,1-diethylurea is heated to 80°–90° C. in 4 ml of DMF with 4 ml of triethylamine, 4 mg of copper(I) iodide, 8 mg of palladium(O) tetrakis(triphenylphosphine) and 112 mg of 4-cyanophenylacetylene for 2 hours. After evaporation, the mixture is distributed in ethyl acetate and saturated sodium bicarbonate solution, and the organic phase is washed with saturated sodium chloride solution. After chromatography over silica gel with methylene chloride:ethanol=10:1, 87 mg of 3-[2-(4-cyanophenylethynyl)-6-methyl-8α-ergolinyl]-1,1-diethylurea is obtained, mp 150°–151° C., $[\alpha]_D = +139.5°$ (c=0.2; pyridine).

The following compounds are prepared analogously:
3-[2-(3-methylphenylethynyl)-6-methyl-8α-ergolinyl]-1,1-diethylurea,
3-[2-(2-methylphenylethynyl)-6-methyl-8α-ergolinyl]-1,1-diethylurea,
3-[2-(4-chlorophenylethynyl)-6-methyl-8α-ergolinyl]-1,1-diethylurea.

EXAMPLE 4

3-[2-(4-Methoxyphenethyl)-6-methyl-8α-ergolinyl]-1,1-diethylurea 50 mg of 3-[2-(4-methoxyphenethynyl)-6-methyl-8α-ergolinyl]-1,1-diethylurea in 20 ml of ethanol is combined with a spatula tip of Raney nickel and hydrogenated for one hour at room temperature and under hydrogen normal pressure. After the product has been filtered off from the catalyst, it is recrystallized from ethyl acetate/hexane, thus obtaining 40 mg of 3-[2-(4-methoxyphenethyl)-6-methyl-8α-ergolinyl]-1,1-diethylurea, mp 147°–149° C., $[\alpha]_D = +4.2°$ (c=0.2; pyridine).

EXAMPLE 5

3-(9,10-Didehydro-6-methyl-2-phenylethynyl-8α-ergolinyl)-1,1-diethylurea 150 mg of 3-(9,10-didehydro-2-bromo-6-methyl-8α-ergolinyl)-1,1-diethylurea is heated to 90° C. for 6 hours in 2 ml of dimethylformamide with 5 mg of copper(I) iodide, 15 mg of palladium(O) tetrakis(triphenylphosphine), 4 ml of triethylamine, and 0.12 ml of phenylacetylene; after filtration over kieselguhr, the mixture is heated once more to 90° C. with 5 mg of copper(I) iodide, 15 mg of palladium(O) tetrakis(triphenylphosphine), and 0.2 ml of phenylacetylene for 3 hours, concentrated, distributed in methylene chloride as well as saturated sodium bicarbonate solution, and the organic phase is washed with saturated sodium chloride solution. After chromatography over silica gel with methylene chloride:ethanol=10:1 and recrystallization from ethanol/hexane, 50 mg of 3-(9,10-didehydro-6-methyl-2-phenylethynyl-8α-ergolinyl)-1,1-diethylurea is obtained, mp 229°–231° C., $[\alpha]_D = +195.8°$ (c=0.23; pyridine).

EXAMPLE 6

3-(6-Methyl-2-phenylethynyl-8α-ergolinyl)-1,1-diethylthiourea

At −12° C., 200 mg of 3-(6-methyl-2-phenylethynyl-8α-ergolinyl)-1,1-diethylurea is combined in 15 ml of methylene chloride with 0.13 ml of phosphorus oxychloride. The reaction mixture is allowed to warm up to room temperature within one hour and is agitated at this temperature for 16 hours. After evaporating the methylene chloride, the mixture is extracted under ether with stirring, suctioned off, and dried over KOH pellets under vacuum. The mixture is then combined at −10° C. with a solution of 245 mg of potassium xanthate in 15 ml of acetonitrile and additionally stirred for 2 hours at room temperature. After evaporation, the mixture is distributed in ethyl acetate/saturated sodium bicarbonate solution, and the organic phase is washed with saturated sodium chloride solution. After chromatographing twice over silica gel, first with the eluent methylene chloride/ethanol=19:1 and secondly with 10:1 and recrystallization from ethanol/hexane/ethyl acetate, 60 mg of 3-(6-methyl-2-phenylethynyl-8α-ergolinyl)-1,1-diethylthiourea is obtained, mp 219°–220° C.

$[\alpha]_D = +195.8°$ (c=0.23; pyridine).

3-(6-Methyl-2-phenethyl-8α-ergolinyl)-1,1-diethylthiourea is prepared analogously.

EXAMPLE 7

3-(6-Methyl-2-phenylethenyl-8α-ergolinyl)-1,1-diethylurea 200 mg of 3-(6-methyl-2-phenylethynyl-8α-ergolinyl)-1,1-diethylurea is added to a mixture, prehydrogenated at room temperature and normal pressure, of 150 mg of palladium/barium carbonate (10% strength) in 30 ml of a solvent mixture of 10 parts of hexane, 2 parts of pyridine, and 1 part of methanol, and hydrogenation is performed up to a steep rise of the curve. After filtering off from the catalyst, the mixture is concentrated and chromatographed over silica gel with ethyl acetate:ethanol=2:1, thus obtaining, after recrystallization, 50 mg of 3-(6-methyl-2-phenethenyl-8α-ergolinyl)-1,1-diethylurea as a mixture of the Z- and E-compounds.

EXAMPLE 8

Under argon, 160 mg of 3-(6-methyl-2-phenethynyl-8α-ergolinyl)-1,1-diethylurea is combined in 15 ml of absolute toluene with 3.5 ml of an approximately 1.2-molar DIBAL-H solution in toluene. After 10 minutes of agitation at room temperature, the mixture is heated for 2 hours to 80° C. After cooling, the mixture is introduced under a protective gas into a 1N aqueous hydrochloric acid solution, stirred for 10 minutes, adjusted to be alkaline with ammonia solution, suctioned off over kieselguhr, and thoroughly rinsed with ethyl acetate. The organic phase is dried, concentrated, and recrystallized from ethyl acetate/hexane.

Yield: 89 mg of 3-(6-methyl-2-E-phenethenyl-8α-ergolinyl)-1,1-diethylurea, $[\alpha]_D^{25} = +123°$ (c=0.2; pyridine).

We claim:

1. A 2-Substituted ergoline compound of the Formula

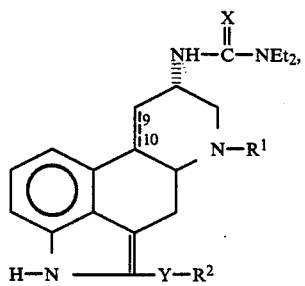

wherein
X is an oxygen or sulfur atom,
$R^1$ is a lower alkyl group,
Y is a sulfur atom, S—CH$_2$—, or C$_2$H$_4$—, is phenyl, pyridinyl, thiophenyl, furanyl, pyrimidinyl, imidazolyl, pyrazolyl or one of the preceding substituted on a carbon atom by a C$_{1-2}$-alkyl, C$_{1-2}$-alkoxy, nitrile, nitro, amino, C$_{1-2}$-alkylamino, carbonylamino or halo group, and
C$_9$---C$_{10}$ is a CC-single or a CC-double bond and, if C$_9$---C$_{10}$ means a CC-single bond, the hydrogen atom in the 10-position is the α-location,
or a pharmaceutically acceptable acid addition salt thereof, wherein, if X is an oxygen atom, $R^1$ is methyl and C$_9$---C$_{10}$ is a single bond, Y—R$^2$ does not mean —C$_2$H$_4$-phenyl.

2. 1,1-Diethyl-3-(6-methyl-2-phenylthio-8α-ergolinyl)urea,
3-(2-benzylthio-6-methyl-8α-ergolinyl)-1,1-diethylurea,
3-(9,10-didehydro-6-methyl-2-phenylthio-8α-ergolinyl)-1,1-diethylurea,
3-(2-benzylthio-9,10-didehydro-6-methyl-8α-ergolinyl)-1,1-diethylurea,
1,1-diethyl-3-(6-methyl-2-phenylthio-8α-ergolinyl)thiourea,
3-[6-methyl-2-(thien-2-ylethynyl)-8α-ergolinyl]-1,1-diethylurea,
3-[6-methyl-2-(3-pyridinylethynyl)-8α-ergolinyl]-1,1-diethylurea,
3-[2-(4-methoxyphenylethynyl)-6-methyl-8α-ergolinyl]-1,1-diethylurea,
3-[2-(4-cyanophenylethynyl)-6-methyl-8α-ergolinyl]-1,1-diethylurea,
3-[2-(4-methoxyphenethyl)-6-methyl-8α-ergolinyl]-1,1-diethylurea,
3-(9,10-didehydro-6-methyl-2-phenylethynyl-8α-ergolinyl)-1,1-diethylurea,
3-(6-methyl-2-phenylethynyl-8α-ergolinyl)-1,1-diethylthiourea,
3-(6-methyl-2-phenylethenyl-8α-ergolinyl)-1,1-diethylurea.

3. A compound of claim 1, wherein $R^1$ is C$_{1-6}$-alkyl.

4. A compound of claim 3, wherein $R^1$ is methyl, ethyl, isopropyl, n-propyl, n-butyl, isobutyl or tert-butyl.

5. A pharmaceutical composition comprising a neuroleptically effective amount of a compound of claim 1 and a pharmaceutically acceptable carrier.

6. A pharmaceutical composition comprising a neuroleptically effective amount of a compound of claim 3 and a pharmaceutically acceptable carrier.

7. A pharmaceutical composition comprising a neuroleptically effective amount of a compound of claim 1 and a pharmaceutically acceptable carrier.

8. A method of treating psychosis in a patient in need of such treatment comprising administering thereto a neuroleptically effective amount of a compound of claim 1, 9. A method of treating schizophrenia in a patient in need of such treatment comprising administering thereto a neuroleptically effective amount of a compound of claim 1.

10. A method of claim 9, wherein the effective amount is 0.1 to 10 mg.

* * * * *